United States Patent
Monceau et al.

(10) Patent No.: US 7,273,316 B2
(45) Date of Patent: Sep. 25, 2007

(54) DEVICE AND METHOD FOR THERMOGRAVIMETRICALLY TESTING THE BEHAVIOR OF A SOLID MATERIAL

(75) Inventors: Daniel Monceau, Nailloux (FR); Jean-Claude Salabura, Castanet (FR)

(73) Assignee: Institut National Polytechnique de Toulouse, Toulouse Cedex (FR)

( * ) Notice: Subject to any disclaimer, the term of this patent is extended or adjusted under 35 U.S.C. 154(b) by 38 days.

(21) Appl. No.: 10/543,149

(22) PCT Filed: Jan. 16, 2004

(86) PCT No.: PCT/FR2004/000090

§ 371 (c)(1),
(2), (4) Date: Jul. 25, 2005

(87) PCT Pub. No.: WO2004/068102

PCT Pub. Date: Aug. 12, 2004

(65) Prior Publication Data

US 2006/0120431 A1    Jun. 8, 2006

(30) Foreign Application Priority Data

Jan. 23, 2003   (FR) .................................. 03 00742

(51) Int. Cl.
*G01N 25/00* (2006.01)
*G01K 13/00* (2006.01)
(52) U.S. Cl. .......................... 374/14; 374/142; 374/45; 374/43
(58) Field of Classification Search .................. 374/14; 436/908
See application file for complete search history.

(56) References Cited

U.S. PATENT DOCUMENTS 4,304,118 A    12/1981    Bartha et al.

(Continued)

FOREIGN PATENT DOCUMENTS

| EP | 0 779 510 | 6/1997 |
|---|---|---|
| GB | 2 212 038 | 7/1989 |
| WO | WO 01/34290 | 5/2001 |

OTHER PUBLICATIONS

Singh Raman R K et al:, "The Stability of Oxide Scale and Oxidation Behaviour of 2 CR-1MO Steel During Thermal Cycling" Materials at High Temperatures, Butterworth Heinemann, Guildford, GB, vol. 10., Nos. 3, 1992, pp. 171-176, XP000486910, ISSN: 0960-3409, p. 171, colonne 2, ligne 4-ligne 14; figure 1, p. 172, colonne 1, dernier alinea—colonne 2, alinea 1; figure 3.

(Continued)

*Primary Examiner*—Diego Gutierrez
*Assistant Examiner*—Mirellys Jagan
(74) *Attorney, Agent, or Firm*—Young & Thompson

(57) ABSTRACT

A method for thermogravimetrically testing the behavior of a solid material in the presence of a controlled gaseous atmosphere, characterized in that a plurality of samples (10) are placed in the presence of the gaseous atmosphere inside the same controlled atmosphere furnace (4); each sample is associated with a scale (38) proper thereto; the samples (10) undergo predetermined successive thermal cycles each including a heating step during which the samples are directly heated (by radiation or induction) and a cooling step during which the weight of each sample is independently measured and recorded in a continuous manner during at least one predetermined period such as a high temperature level during the heating step of each thermal cycle. The invention also relates to a device for carrying out the method.

34 Claims, 6 Drawing Sheets

U.S. PATENT DOCUMENTS

| | | | |
|---|---|---|---|
| 4,606,649 A * | 8/1986 | Mikhail | 374/10 |
| 4,874,948 A | 10/1989 | Cielo et al. | |
| 5,165,792 A * | 11/1992 | Crowe et al. | 374/10 |
| 5,215,377 A * | 6/1993 | Sugano | 374/14 |
| 5,306,087 A * | 4/1994 | Nakamura et al. | 374/14 |
| 5,368,391 A | 11/1994 | Crowe et al. | |
| 6,336,741 B1 | 1/2002 | Blaine | |
| 6,903,281 B2 * | 6/2005 | Dalmia et al. | 177/212 |
| 2004/0173142 A1 * | 9/2004 | Willis | 117/200 |
| 2005/0018746 A1 * | 1/2005 | Reader et al. | 374/14 |

OTHER PUBLICATIONS

Spinceana D et al:, Surface dynamics in tin doixide-containing catalysts II. Competition between water and oxygen adsorption on poloycrystalline tin dioxide:, Sensors and Actuators B, Elsevier Sequoia S.A., Lausanne, CH, vol. 30, No. 1, 1996, pp. 35-41, XP004006295, ISSN: 0925-4005, p. 36, alinea 2; figures 3A 3B.

* cited by examiner

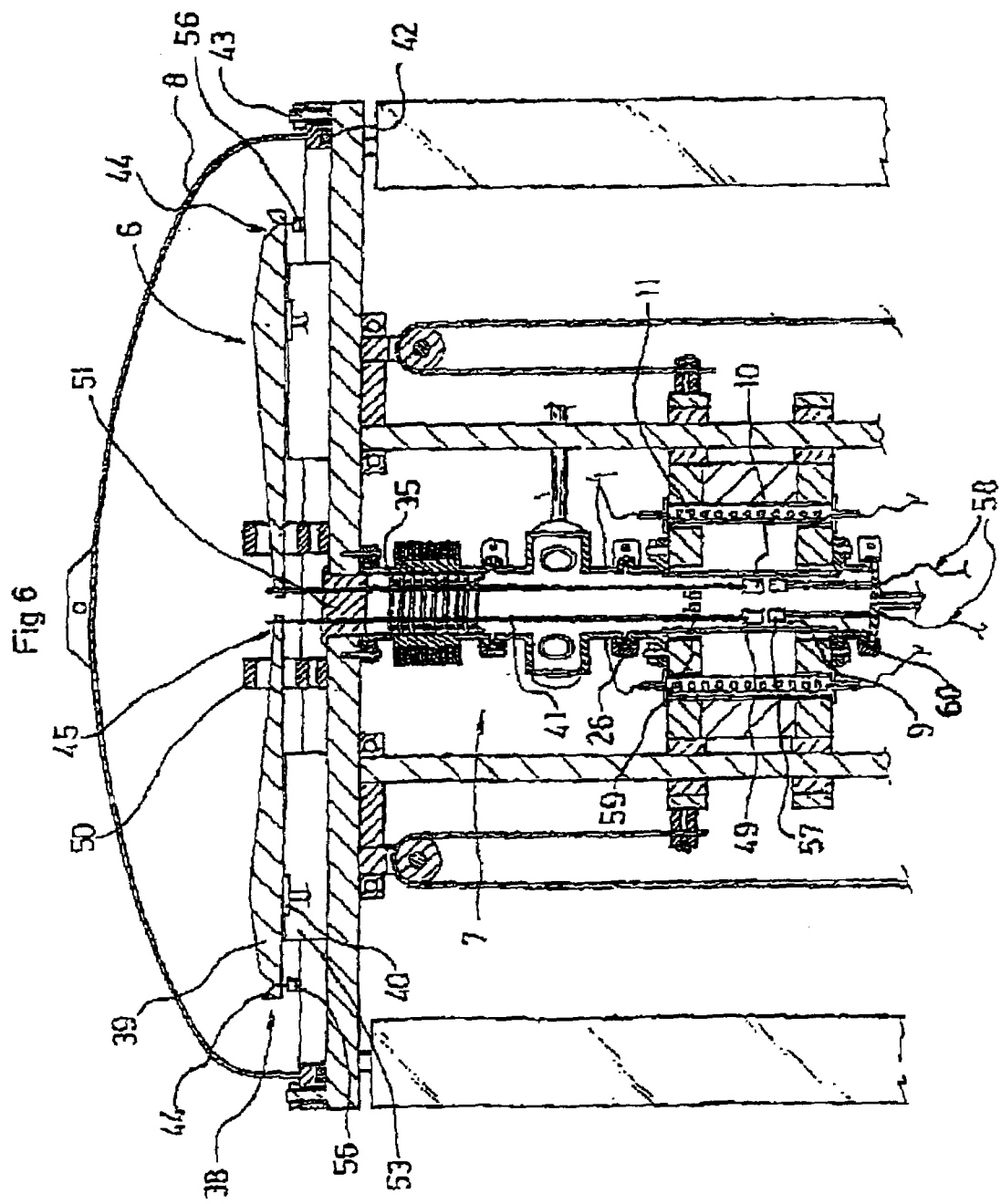

DEVICE AND METHOD FOR THERMOGRAVIMETRICALLY TESTING THE BEHAVIOR OF A SOLID MATERIAL

FIELD OF THE INVENTION

The invention relates to a device and method for thermogravimetrically testing the behaviour of a solid material subjected, in the presence of a gaseous atmosphere, to considerable variations in temperature.

BACKGROUND OF THE INVENTION

The majority of materials (metal alloys, ceramics, concretes, etc.) oxidise under the effect of an elevated temperature in the presence of a gaseous atmosphere. This phenomenon of oxidation is amplified and becomes damaging when the material is subjected to considerable cyclic variations in temperature: during the first cycles, exposure of the material to high temperatures causes the formation of a protective oxide layer (transitory oxidation phase), which grows until it reaches a critical thickness above which any cooling to which the material is subjected causes flaking of the protective oxide layer; during subsequent cycles, cooling operations to which the material is subjected cause the protective oxide layer to break up, and successive oxidations at high temperature of the surface of the material thus exposed deplete it of elements permitting the formation of the protective oxide, to exhaustion; cyclic exposure of the material to high temperatures then manifests itself as in-depth oxidation of the material (formation of metal oxide sub-layers, which flake during the cooling phases), which thus attacks the material until it breaks.

In addition to oxidation of the material, exposure of a material to high temperatures can also cause phenomena of corrosion, passivation or adsorption, which manifest themselves as a gain in mass of the material, or phenomena of decomposition, dehydration, pyrolysis, combustion or dehydroxylation, which manifest themselves as a loss in mass of the material. These phenomena can be observed and studied by thermogravimetry.

The thermogravimetric study of the behaviour of a material subjected, in the presence of a gaseous atmosphere, to considerable variations in temperature is fundamental to many industries: aviation (gas turbines, especially of aircraft engines), the automotive industry (exhaust pipes, catalytic converters, etc.), chemical engineering (chemical and petrochemical factory reactors), the nuclear industry, the electrical industry (thermal generators), etc. It allows evaluation of, inter alia, the resistance of a material to thermochemical attacks, its lifetime, the risks of cracking, the maximum possible use temperature of the material, etc., and makes it possible to work at developing new, higher-performance materials which are capable of withstanding higher use temperatures. The thermogravimetric study of the behaviour of a material at high temperature is also of interest ecologically: increasing the use temperatures of materials results in a greater efficiency of the industrial processes in which the materials are involved, and a subsequent reduction in energy consumption, $CO_2$ emissions, etc.

During use, materials undergo attacks of various origins: attacks of thermal and/or chemical origin (high-temperature oxidation, cyclic oxidation, corrosion, decomposition, dehydration, etc.), mechanical stresses, cyclic thermo-mechanical fatigue, etc. These various factors interact in a complex manner. And there is at present no laboratory test that is capable of reproducing all these factors at reasonable cost and in reduced times.

For a material subjected to elevated temperatures (from 400 to 1800° C.) and/or to considerable variations in temperature, thermal phenomena (and especially the phenomena of oxidation and/or corrosion at high temperature, depending on the composition of the gaseous atmosphere) often prove to be the most important. For that reason, the lifetime of a material subjected to such use conditions is evaluated on the one hand by means of simplified and "accelerated" thermogravimetric tests, which allow measurement of the effects of exposure (isothermal or cyclic) of the material to high temperatures for a given period of time, and on the other hand by means of mathematical simulation models which, when applied to the experimental results of the preceding thermogravimetric tests, make it possible to simulate and extrapolate not only the long-term action of cyclic high-temperature exposure (as a function of the actual use conditions of the material—chemical composition of the atmosphere, maximum temperature of the material, time of exposure to high temperature for each cycle, number of cycles, rate of heating, rate of cooling, etc.—which are often different from the test conditions), but also the effects of other possible factors (mechanical, thermo-mechanical, etc.), the interaction of the various factors, the random nature of certain phenomena, a statistical modulation of the experimental results.

THE PRIOR ART

Two types of thermogravimetric test are known at present:
  isothermal thermogravimetric tests, in which a sample of material is placed in a furnace and exposed to an elevated temperature corresponding to a potential use temperature of the material, and the gain in mass (or in weight) of the material following this exposure is measured (the term "gain" denoting a relative gain: it is positive in the case of an increase in mass and negative in the case of a loss of mass). In the case of an oxidation test, measurement of the gain in mass of the sample provides information regarding the amount of oxide formed. In all cases, measurement of the gain in mass of the sample is carried out either by means of a "conventional" balance at ambient temperature (the sample is in this case removed from the furnace beforehand and placed on the balance, and the test is described as discontinuous), or by means of a thermobalance such as a SETARAM® electric resistance thermobalance (the resistance furnace and the balance being combined in a single device) while the sample is still in the furnace (such a test is described as continuous). Continuous isothermal tests are more reliable than discontinuous tests: the handling, cooling and change in hygrometry which the sample undergoes within the scope of a discontinuous test, during its transfer from the furnace to the balance, cause an effect of premature flaking of the oxide layer and losses of oxide particles, as well as charging of the sample with moisture, which falsify the mass-gain measurements;
  cyclic thermogravimetric tests, in which a sample is subjected to cyclic variations in temperature, each cycle comprising a heating step in a furnace and a cooling step outside the furnace, and the weight of the sample is measured periodically, between two cycles. These tests are carried out by means of a combustion or electric resistance furnace. Each cooling step is carried out at ambient temperature, outside the furnace, from which the sample is removed manually or automatically. The sample is weighed regularly outside the furnace, after a given number of cycles (by way of example, the sample is subjected to successive 2-hour cycles and is measured once per day, that is to say approximately every 11 cycles).

The major disadvantage of isothermal tests is that they do not reproduce realistic use conditions for industrial materials. In fact, it is rare that materials are subjected, during use, to constant temperatures throughout their lifetime. In the large majority of cases, the materials are subjected to cyclic variations in temperature (owing to the discontinuous use of industrial installations). However, the effect, mentioned hereinabove, of cyclic cooling on the durability of the material is fundamental. Interpreting the results of isothermal tests with a view to predicting the effects of cyclic oxidation/corrosion (or other attack) is difficult. The value and reliability of isothermal tests are consequently relatively limited.

By contrast, cyclic tests make it possible to take into consideration the effects of cooling to which the material is subjected in the process of oxidation/corrosion (or other phenomenon). However, the known cyclic tests do not allow the re-creation of test conditions which are similar, or at least are capable of permitting reliable extrapolation, to the actual use conditions of the material being tested. Moreover, the known cyclic tests are discontinuous tests (weight measurements are carried out outside the furnace) and as such have the same disadvantages as the discontinuous isothermal tests. These tests must therefore be interpreted with caution. The results that they provide are, moreover, insufficient to permit fine analysis of the phenomena in question. Moreover, the tests take a long time to carry out and require the frequent intervention of a technician (especially to carry out the operations of weighing the samples of material).

In addition, the known isothermal tests, when they are discontinuous, only provide the net gain in mass (gain in mass of the sample alone) following the exposure to high temperature. Whatever the final purpose of the test (study of oxidation, dehydration, etc.), this parameter is insufficient for permitting analysis of the phenomena in question and evaluation of the lifetime of the material. In the case of an oxidation test in particular, measurement of only the net gain in mass following the exposure to high temperature does not allow the increase in mass of the sample due to adsorption of oxygen (formation of the oxide) to be separated from the loss in mass due to flaking of the oxide. The information provided by the test therefore remains inadequate.

Likewise, the known cyclic tests, which are discontinuous, only provide either the net gain in mass between two cycles when the sample is suspended in the furnace by means of a hook, or both the net gain in mass and the gross gain in mass (variation in mass both of the sample and of the oxide lost by flaking) between two cycles when the sample is placed in a crucible inside the furnace. The disadvantages of the first method have been discussed hereinabove. The second method provides important additional information but raises a number of experimental problems: it is impossible to obtain rates of heating/cooling of the sample that are elevated—and a fortiori realistic—inside a crucible; the presence of the crucible alters the gaseous environment (which cannot be homogeneous) of the sample; the variation in mass of the crucible itself reduces the accuracy of the measurements; the handling of the sample that is necessary to measure its net gain in mass (removal from the crucible) risk damaging the layer of oxide and falsifying the measurements. These comments are also applicable to any test other than an oxidation test.

It is to be noted that there also exist known methods for characterising a material (determining its chemical composition—nature and proportion of its constituents, its degree of polymerisation and/or crosslinking if it is a polymer, etc.) which use thermogravimetric techniques to detect the changes undergone by the material (revealed by the variations in weight of the sample) when it is subjected to an increase in temperature. By determining the temperatures at which such changes occur and the quantity of material lost or gained by the sample, it is possible to determine the nature of its constituents.

It is not the aim of these known characterisation methods, nor do they make it possible, to predict the behaviour of a material subjected, during use, to an aggressive gaseous atmosphere and to pronounced variations in temperature. Furthermore, none of these methods provides for the material to be subjected to predefined temperature cycles in order to reproduce or model the actual use conditions of the material, with a view to studying the phenomena that occur during oxidation and/or corrosion and/or dehydration, etc. of the material and to predict its lifetime. And the devices they use are unsuitable for this type of test.

Nevertheless, mention may be made, by way of information, of U.S. Pat. No. 5,638,391, which describes a characterisation method in which the rate of heating of the sample is constantly regulated (automatic control) as a function of the measured weight, in order to impose a very low rate (less than 10° C./minute) during changes and a higher rate (from 50 to 100° C./minute) outside changes, with a view to achieving better resolution (separation of the possible changes occurring at similar temperatures) and a reduction in the duration of the test. The thermal test conditions (temperatures, rates of heating/cooling, duration, etc.) are therefore defined as the test progresses, according to the weight of the sample. Real use conditions of the material are not simulated at all. WO 01/34290 describes a device for synthesising and characterising an individual chemical (polymer) and/or biological compound from a combinatory library, which comprises rows of synthesis crucibles arranged in parallel lines. Each crucible is subjected to a rise in temperature, obtained by indirect heating means such as heating channels running between the crucibles, while an alternating voltage is applied to an electrode which extends beneath a flexible membrane having a reflective face, which forms the base of the crucible. The resulting alternating electric field causes the membrane to vibrate, the amplitude of the vibration, measured by an optical sensor beneath the membrane, depending on the mass of polymer contained in the crucible. EP 779 510 describes an apparatus for analysing the composition of a gas, comprising a sensor or a row of sensors. Each sensor is composed of an piezoelectric crystal anode enclosed in a casing for receiving a volume of gas, which anode is covered with a metal capable of adsorbing the particles of a given component (according to the nature of the metal coating) of the gas by electrostatic precipitation, then releasing the adsorbed particles by oxidation under the effect of heat. The piezoelectric anode allows the variations in weight of the metal coating to be determined, by measurement of its oscillation frequency, when it adsorbs or releases particles of gas. Such an apparatus is designed specifically for testing gases and is not suitable for testing the behaviour of solid materials, in particular because it does not have means for receiving and measuring the weight of a sample of solid material.

OBJECT OF THE INVENTION

The invention aims to remedy these disadvantages by proposing principally a method for thermogravimetrically testing the behaviour of a material when it is subjected to pronounced variations in temperature in the presence of a controlled gaseous atmosphere, which method is more reliable, more accurate and more rapid than the known test methods. The invention aims also to provide a device for carrying out such a method.

The object of the invention is especially to provide a method and a device allowing the material to be tested under thermal conditions (temperature of the material, rates of heating and cooling, duration of the thermal cycles, etc.) which are suitable for permitting a reliable prediction of the behaviour of the material under its actual use conditions.

In particular, it is an object of the invention to propose a method in which the material is tested under thermal conditions that are very similar to its actual use conditions, and a device capable of reproducing such thermal conditions. Another object of the invention is to propose a method in which the material is tested under so-called environmental conditions (pressure and chemical composition of the atmosphere in which it is carried out) which are similar to its actual use conditions, and a device capable of reproducing such environmental conditions.

Another object of the invention is to provide a method and a device which make it possible to evaluate and accurately monitor, in each thermal cycle, the evolution of the behaviour of the material and, especially, in the case of an oxidation test, the amount of oxide formed, the oxidation kinetics, the amount of oxide lost by flaking, the flaking kinetics, the average thickness of the remaining layer of oxide, its adherence to the metal, etc, without these evaluations requiring additional handling of the material or prolonging the duration of the test.

Another object is to provide a method and a device which make it possible to evaluate with greater reliability the statistical behaviour of a material subjected to considerable variations in temperature in the presence of a given gaseous atmosphere. In particular, the invention aims to provide a device which allows the same experiment to be reproduced several times under identical environmental and thermal conditions.

Another object of the invention is to provide a compact test device.

The invention also aims to reduce considerably the cost and the duration of a test without prejudicing the accuracy, reliability and pertinence of the test.

SUMMARY OF THE INVENTION

The invention relates to a method for thermogravimetrically testing the behaviour of a solid material in the presence of a controlled gaseous atmosphere, wherein:

a plurality of samples are placed in the presence of said gaseous atmosphere inside the same controlled-atmosphere furnace, each sample has its own associated balance having an error of less than 100 µg; it is to be noted that the term "balance" is understood as meaning any means of measuring weight or mass or of measuring the variation in weight or mass, without any exclusion regarding the type of balance (so-called beam balance, Roberval balance, electronic weighing cell, displacement-measuring optoelectronic sensor, voltage-measuring electronic sensor, etc.), the samples are subjected to predetermined successive thermal cycles each comprising a heating step, during which the samples are heated directly, and a cooling step, during which the samples are not heated; it is to be noted that the expression "the samples are heated directly" means that the samples are heated in a direct manner by radiation or induction, for example, in contrast to indirect heating methods (using heating means of the thermal electric resistance, combustion gas type, etc.), which consist in heating the atmosphere surrounding the samples in order to increase their temperature, the weight of each sample is measured and recorded independently, in a continuous manner, for at least a predetermined period during the heating step of each thermal cycle. It is to be noted that the measured weight corresponds to the absolute weight of the sample if the balance is adjusted to zero when empty, or—preferably—to a relative weight of the sample relative to its initial weight if the balance is adjusted to zero at the start of the test, provided with the sample.

In particular, the weight of each sample is measured and recorded in a continuous manner at least during a high-temperature stage of the heating step of each thermal cycle. It is to be noted that it is equally possible to measure and record the weight of each sample during a period of the cooling step, or even throughout the entirety of the test. However, in the particular case of an oxidation test, the inventors have shown that a study of the variations in weight (or in mass) of each sample during a high-temperature stage of the heating step is sufficient on its own for describing the oxidation phenomena sensitively and reliably, as will be explained hereinbelow.

According to the invention, therefore, and contrary to the known cyclic tests (which provide phases of cooling of the sample in the open air, outside the furnace and away from any controlled atmosphere), the samples are placed in a controlled-atmosphere furnace in order to be subjected to thermal cycles and are not removed therefrom until the end of the cyclic test. They are therefore exposed, permanently (during each cycle and between cycles), for the entire duration of the test, to a controlled gaseous atmosphere. The samples can thus be maintained and observed in an environment (pressure and chemical composition of the atmosphere surrounding them) that has been created so as to correspond, as closely as possible, to their actual use environment.

In addition, contrary to the known cyclic tests, the weighing operations are carried out without handling of the samples by a technician or even by the device. The samples are not subjected to any mechanical stress which might modify their mass in an undesirable manner and in particular damage the oxide formed and facilitate flaking thereof. Consequently, it is possible accurately to observe the effects of only the thermal cycles on the material; and the results obtained are particularly reliable.

Moreover, the weighing operations are carried out automatically during the thermal cycles (and not between two thermal cycles), without interrupting said cycles. In addition to the possibility of carrying out successive thermal cycles in a continuous manner (like the actual cycles to which the material is subjected in use), an appreciable and significant gain in terms of time is achieved.

Furthermore, according to the invention and contrary to all the known cyclic tests, which provide the gain in mass (net or gross) in a limited manner between two cycles, the weight of each sample present in the furnace is measured and recorded continuously at least over a given period during the heating step, and especially during a high-temperature stage of that step. From these measurements it is possible to deduce the values of a large number of rich information parameters, some of which were previously inaccessible, such as—in the case of an oxidation test—the exact amount of oxide formed in each cycle on each sample (given by the gain in mass of the sample during the high-temperature stage), the kinetics of formation of the oxide (and the inventors have shown that this gives information regarding the nature of the oxide formed), the exact amount of oxide lost by flaking in each cycle by the sample (given by the difference in weight of the sample between the end of a high-temperature stage and the start of the following high-temperature stage), the thickness of the layer of oxide formed (obtained by calculation), etc. And this information is obtained without handling the sample and solely by weighing the sample alone (and not the oxide lost by flaking) for a predetermined period during the heating step (chosen according to the phenomena to be studied and according to the material). In the case of an oxidation test, this period advantageously corresponds to a high-temperature stage, the inventors having shown that the formation of the oxide on the material occurs substantially during such a stage. The choice of this period has another advantage: at a substantially constant temperature, the thermal currents and the effect of the variations in the buoyancy to which the samples are subjected are negligible; the weight measurements are therefore more reliable. The exploitation of the weight measurement results of the samples outside such stages is more delicate and proves to be of little use.

The method according to the invention accordingly permits finer and more reliable analysis of cyclic oxidation/corrosion phenomena at high temperature. In particular, it allows the evolution of the behaviour of the material to be observed not only during one thermal cycle but also and especially from one cycle to another, at various stages of the oxidation method, and allows the lifetime of the material to be predicted in an accurate and reliable manner. These comments are applicable whatever the phenomenon studied (decomposition, pyrolysis, dehydration, etc.).

In addition, contrary to all the known tests using thermobalances (isothermal tests), the method according to the invention consists not only in subjecting the material to thermal cycles, but also in weighing, simultaneously and independently, a plurality of samples placed in the same gaseous atmosphere, that is to say placed under strictly identical environmental conditions. The samples are weighed by means of independent balances which are able to operate concomitantly, each balance measuring the weight of a single sample with an error of less than 100 µg. By means of the method according to the invention it is therefore possible to reproduce the same experiment several times under identical conditions, in a limited time, at reduced cost and using reduced means but with a high degree of accuracy. Consequently, it is possible to carry out reliable statistical studies on the measurement results obtained.

It is to be noted, moreover, that the known thermobalances, which are designed exclusively for carrying out isothermal tests, do not allow exploitable cyclic tests to be carried out. In fact, the rates of heating and cooling which can be obtained inside the furnace of a known thermobalance are low (of the order of 60° C./minute for heating and 30° C./minute for cooling) and, for the large majority of materials, are out of proportion relative to the actual rates of heating and cooling of the material during use (in particular in the case of an aviation material). This is one of the reasons why the known thermobalances are unsuitable for cyclic tests.

The invention also consists in using means for heating the samples directly. Such means offer rates of heating and cooling of the samples that are superior to the indirect heating means used in the methods of the prior art, and allow thermal cycles comprising very short phases of rise and fall in temperature to be carried out. The method and the device according to the invention are suitable for the most demanding applications, such as aviation applications.

Advantageously and according to the invention, one or more of the following operations are carried out:

in each thermal cycle, the samples are heated so that their temperature is from 400 to 1800° C. at least during a high-temperature stage of the heating step, and especially greater than 1100° C. at least during such a stage;

in each thermal cycle, the samples are heated at a rate of heating greater than 300° C./minute (in other words, the samples are heated in such a manner as to increase their temperature by more than 300° C. in one minute), or even greater than 1000° C./minute;

in each thermal cycle, the samples are cooled at a rate of cooling greater than 100° C./minute (in other words, the samples are cooled in such a manner as to lower their temperature by more than 100° C. in one minute);

according to the nature and intended use of the material being tested, the samples are subjected to a number of successive thermal cycles of from 10 to 3000;

the samples are subjected to thermal cycles each comprising a heating step, which consists of a phase of rise in temperature having a duration of less than 5 minutes and a high-temperature stage having a duration of the order of 60 minutes, and a cooling stage, which consists of a phase of fall in temperature having a duration of less than 10 minutes and a low-temperature phase having a duration of from 0 to 15 minutes.

By way of example, in the case of a tested material of the superalloy type intended for aviation applications (turbines, nozzles, etc.), the samples are subjected to a number of thermal cycles varying from 300 to 3000, each cycle comprising a phase of rise in temperature of at least 2 minutes, a high-temperature stage of approximately 60 minutes, during which the samples are maintained at a temperature of from 1100° C. to 1500° C., and a phase of fall in temperature of approximately 4 minutes, which allows the samples to be returned to a temperature of from 100 to 200° C., and a low-temperature stage (from 100 to 200° C.) for a period of from 0 to 15 minutes.

In the case of a ceramics-type material, the samples are brought to 1800° C. within a period of less than 3 minutes (phase of rise in temperature) and maintained at that temperature during the high-temperature stage.

In the case of a material of the steel or alloy type intended for automotive pipework applications (exhaust pipe) or for the chemical industry, the temperature of the high-temperature stage is of the order of 500° C., the temperature of the low-temperature stage is from 10 to 30° C. and the duration of the high- and low-temperature stages may vary, according to the application, from several minutes to several hours.

It is to be noted that the thermal cycles of the same cyclic test may be identical or different. In particular, they may have different maximum temperatures and/or different minimum temperatures and/or different durations of the heating step or the high-temperature stage and/or different durations of the cooling step or the low-temperature stage and/or different rates of heating and/or different rates of cooling, etc.

The invention relates also to a device for thermogravimetrically testing the behaviour of a solid material in the presence of a controlled gaseous atmosphere, which device enables the method according to the invention to be carried out. The invention relates especially to a device comprising:
  a furnace with a controlled gaseous atmosphere,
  means for weighing the material placed in the furnace, having an error of less than 100 µg,
  confining means suitable for limiting any disturbance to the weighing means owing to the external environment of the device and/or the controlled gaseous atmosphere of the furnace.

It is characterised in that:
  the furnace is suitable for receiving a number N, which is strictly greater than 1, of samples of the material (that is to say a plurality of samples),
  the furnace comprises means for heating the samples directly, which means are capable of subjecting the samples to successive predetermined thermal cycles each comprising a heating step, during which the samples are heated, and a cooling step, during which the samples are not heated,
  the weighing means comprise N independent balances having an error of less than 100 µg, each balance being capable of measuring and recording the weight of a sample continuously at least during a predetermined period during the heating step of each thermal cycle. In particular, each balance is capable of measuring and recording the weight of a sample continuously at least during a high-temperature stage of the heating step of each thermal cycle.

The expression "direct heating means" denotes means of the radiant or inductive type which are capable of heating the samples of material directly without necessarily heating the atmosphere surrounding them.

The device is preferably star-shaped in its overall structure, at least the balances being arranged in the shape of a star. Such a structure is particularly compact.

Advantageously and according to the invention, this star-shaped structure is suitable for receiving the samples close to one another in a central portion of the furnace. Such a structure allows the samples to be arranged in the central portion of the furnace within a limited volume, the form and dimensions of which facilitate the creation of a homogeneous atmosphere. The samples are therefore subjected strictly to the same atmosphere at all times.

In addition, because the receiving volume for the samples is limited, it is possible, by closing that volume at least partially, to limit the effect on the weighing operation of the gaseous currents due to thermal variations (thermal currents), to a circulation of gas with a view to maintaining or voluntarily changing the controlled atmosphere (supply to the furnace or extraction), until that influence is rendered negligible. This would not be the case in a device in which the samples and their associated balances were aligned in rows, and in which it would be advisable to take those effects into account when studying the behaviour of the material.

Advantageously and according to the invention, the direct heating means are capable of bringing the samples to a temperature greater than 400° C., and especially greater than 1100° C., or even greater than 1800° C., of heating the samples at a rate of heating greater than 300° C./minute, or even greater than 1000° C./minute, and of cooling the samples at a rate of cooling greater than 100° C./minute. The direct heating means are preferably capable of carrying out thermal cycles each comprising a heating step, which consists of a phase of rise in temperature having a duration of less than 5 minutes and a high-temperature stage having a duration of the order of 60 minutes, and a cooling step, which consists of a phase of fall in temperature having a duration of less than 10 minutes and a low-temperature stage having a duration of from 0 to 15 minutes. The direct heating means are preferably capable of carrying out more than 3000 successive thermal cycles.

In a preferred embodiment of the invention, the furnace comprises:
  at least N high-radiation lamps, such as halogen lamps,
  a receiving chamber for the samples made of a thermal resistant material which is transparent to the radiation of the lamps (visible and/or infra-red and/or ultraviolet radiation, according to the nature of said lamps); in particular, the chamber is made of optical-grade quartz (such a material is transparent to visible radiation and is heated only slightly under the effect of such radiation); it is to be noted that the term "chamber" denotes both the confined space for receiving the samples inside the furnace and the wall (of quartz) delimiting that space,
  a reflective peripheral inner face having a form suitable for defining at least N separate zones of maximum illumination inside the chamber, at the site of which the samples may be placed; the expression "zone of maximum illumination" denotes a convergence zone of the radiation emitted by the lamps and reflected by the inner peripheral face of the furnace.

Advantageously and according to the invention, the peripheral inner face of the furnace forms at least N ellipse portions arranged in the shape of a star, each ellipse having a first focus outside the chamber, called the emitting focus, at the site of which there is arranged a lamp, and a second focus inside the chamber, called the receiving focus, at the site of which a sample of the material may be placed. According to the invention, at least N ellipses have separate receiving focuses. The chamber and the receiving focuses are preferably situated in the central portion of the furnace, and the emitting focuses are situated in the peripheral portion of the furnace. The chamber advantageously has reduced radial dimensions, preferably just sufficient to house the samples.

Such heating means have an advantageous flexibility, especially rates of heating and cooling which can be altered as desired, the rates of heating readily being able to exceed 300° C./minute (and even 1000° C./minute) and the rates of cooling being able to exceed 100° C./minute. They also allow the samples to be brought to very high temperatures (of the order of 1800° C.). They therefore provide the possibility of carrying out different thermal cycles as a function of the nature and intended use of the material being tested, and of reproducing, in the large majority of cases, thermal conditions similar to the actual use conditions of the material.

Advantageously and according to the invention, each balance has an error of less than 10 µg and especially of the order of 1 µg. Advantageously and according to the invention, each balance has a drift of less than 10 µg/h, preferably less than 1 µg/h and especially of the order of 0.1 µg/h.

Advantageously and according to the invention, the balances are mounted on the same support plate. They are preferably arranged above the furnace, and each comprises:
  a balance arm,
  means for measuring a displacement or a force experienced by the balance arm, an aluminium suspension rod which extends substantially vertically and has a lower end which is provided with a platinum hook for attaching a sample and an upper end which is articulated with or fixed to one longitudinal end of the balance arm. The latter is called the measuring end of the balance arm; the other longitudinal end of the balance arm is called the calibrating end.

As explained above, the balances are advantageously arranged in the shape of a star in order to allow the samples to be placed in a central chamber of reduced radial dimensions, in which it is simple to create a controlled homogeneous atmosphere, at reduced cost (use of a small amount of gas, energy saving for producing the vacuum inside the chamber or the introduction and removal of gas, etc.). The balance arms, the longitudinal dimensions of which are greater than the radial dimensions of the chamber, are accordingly preferably arranged in the shape of a star: the balance arm of each balance extends substantially according to a radial direction, for example parallel to the axis of an ellipse of the furnace, so that its measuring end hangs over the central portion of the furnace and the suspension rod carried by that end therefore extends in the central portion of the device at the level of a receiving focus (the calibrating end of the balance arm being in the peripheral portion).

The measuring means of at least one balance, and preferably of each balance, comprise an electronic weighing cell on which the balance arm rests and is fixed. By way of variation, the balance arm rests on a fixed blade, on which it is able to oscillate freely, and the measuring means comprise optoelectronic means for measuring the displacement of a point of the balance arm.

The suspension rods are optionally of the capillary type, that is to say hollow, with two channels permitting the passage of thermocouple wires, such as type S thermocouple wires (platinum/rhodium-plated platinum).

By way of variation, the device comprises means for supporting at least one piece of material (of the same nature as the material being tested), called the control, which support means are suitable for holding the control in the immediate proximity of a sample, preferably beneath the sample and on a receiving focus, and are equipped with means for measuring the temperature inside the control. These temperature-measuring means comprise, for example, thermocouple wires which end inside the control. Contrary to the preceding embodiment, the thermocouple wires here measure precisely the temperature of the material, inside the control, and not the temperature in the vicinity of a sample. In the presence of the direct heating means according to the invention, it is not rare to obtain a temperature difference of about one (or even several) hundred degrees Celsius between the material and the atmosphere immediately surrounding it. This latter embodiment therefore provides a more reliable estimate of the temperature of the samples being tested (by measuring the temperature of the control) and allows more accurate control of the heating means in order to carry out the temperature cycles as predetermined. Furthermore, the presence of thermocouple wires in the suspension rods of the samples can cause not negligible disturbances in the weight measurements of the samples, and it is advisable to evaluate such disturbances and take them into account. The use of a control arranged beneath and in the vicinity of a sample allows this problem to be overcome.

Advantageously and according to the invention, the device comprises support means for N controls, which means are suitable for holding a control beneath each sample, on a receiving focus, and are equipped with means (thermocouple wires ending inside the control) for measuring independently the temperature of each of the controls. It is thus possible to regulate the temperature of each sample in an independent manner, by controlling each lamp in an independent manner.

The furnace is mounted to slide according to a substantially vertical direction between a bottom preparation position, in which it is located beneath the lower end of the suspension rods in order to allow the samples to be attached and/or removed, and a top test position, in which the lower ends of the suspension rods (and the samples which may be attached thereto) extend inside the chamber of the furnace in order to carry out a test.

Advantageously and according to the invention, the confining means comprise:
an upper protective bell which is suitable for covering all the balances and for being fixed in a removable and air-tight manner to the support plate,
a confinement column between the support plate and the furnace, which column is suitable on the one hand for producing an air-tight and removable connection, allowing the suspension rods to pass and be confined, between the support plate and the chamber of the furnace, and on the other hand for producing an air-tight and preferably removable connection to means for generating the controlled gaseous atmosphere. To this end, the column comprises various branches, especially a branch for its connection (in an air-tight and preferably removable manner) to a vacuum pump, a branch for its connection (in an air-tight and preferably removable manner) to a gas inlet pipe and a branch for its connection to a safety valve. In addition to the vacuum pump and the gas inlet pipe for supplying the chamber of the furnace, the means for generating the controlled gaseous atmosphere also comprise a gas outlet pipe which opens at an inner face of the chamber of the furnace, allowing a circulation of gas to be produced inside said chamber from the gas inlet pipe to the gas outlet pipe,
means for limiting gaseous and thermal exchanges between the furnace and the weighing means. Advantageously and according to the invention, the means for limiting gaseous and thermal exchanges comprise a plurality of superposed and distant plates which are integrated into the confinement column above the branches thereof, said plates delimiting a plurality of successive cooling chambers. Each plate is perforated with N holes for the passage of the suspension rods; it preferably has faces of low emissivity. These means advantageously limit on the one hand thermal exchanges between the furnace and the weighing means, so that the temperature beneath the protective bell remains close to ambient temperature (20° C.) and the various measuring (especially electronic) instruments are preserved. On the other hand, they limit gaseous currents (especially of thermal origin) between the furnace and the weighing means, which currents are liable to generate stresses on the weighing instruments and influence the measurements.

The protective bell, the support plate, the confinement column and the chamber of the furnace thus form a confined containment having a controlled atmosphere, inside which the same pressure (but different temperatures) prevails. In fact, the means for limiting gaseous and thermal exchanges according to the invention advantageously permit gaseous exchanges of weak flow between the furnace and the weighing means, allowing the pressures to be equalised between these two parts of the device. An air-tight enclosure for these two parts would have the damaging consequence of generating pressure differences which might falsify the weight measurements of the samples.

Advantageously and according to the invention, each balance also comprises a counterweight, preferably made of an inert material (with respect to the gaseous atmospheres of the different tests to be carried out), fixed to the calibrating end of the balance arm so as to be suspended inside the protective bell. This counterweight remains permanently, from one test to another, inside said bell, in a confined environment. At the start of the test, for each sample attached to a suspension rod, there is advantageously added to said rod (which for that purpose comprises a suitable platinum hook) a tare of an inert material, chosen in order to adjust the balance to zero (which imparts greater accuracy to the weight measurements). Adjustment of the balance is thus carried out without having to open the protective bell. Disturbance of the instruments present beneath the bell and contamination of the atmosphere inside the bell (with dust, undesirable gases, etc.) are thus avoided. The accuracy and reliability of the test are increased thereby, and the time for which the device is immobilised between two tests is reduced considerably.

Advantageously and according to the invention, the furnace comprises a temperature-regulating device of the PID (proportional integral derivative) type or of the predictive and/or self-adaptive type. Such a regulator takes account of past and future evolution to control the heating means in real time.

In addition, the temperature-regulating means of the furnace are advantageously suitable for controlling each lamp independently, especially as a function of the results of the temperature measurement of the samples or of the controls.

The invention relates also to a thermogravimetric test method and device, characterised in combination by all or some of the features mentioned hereinabove and hereinbelow.

BRIEF DESCRIPTION OF THE DRAWINGS

Other aims, features and advantages of the invention will become apparent upon reading the following description, which refers to the accompanying figures showing preferred embodiments of the invention which are given solely by way of example and without implying any limitation and in which:

FIG. 6 is a diagrammatic vertical section of part of another thermogravimetric test device according to the invention.

DETAILED DESCRIPTION OF THE PREFERRED EMBODIMENT

Figure 1:
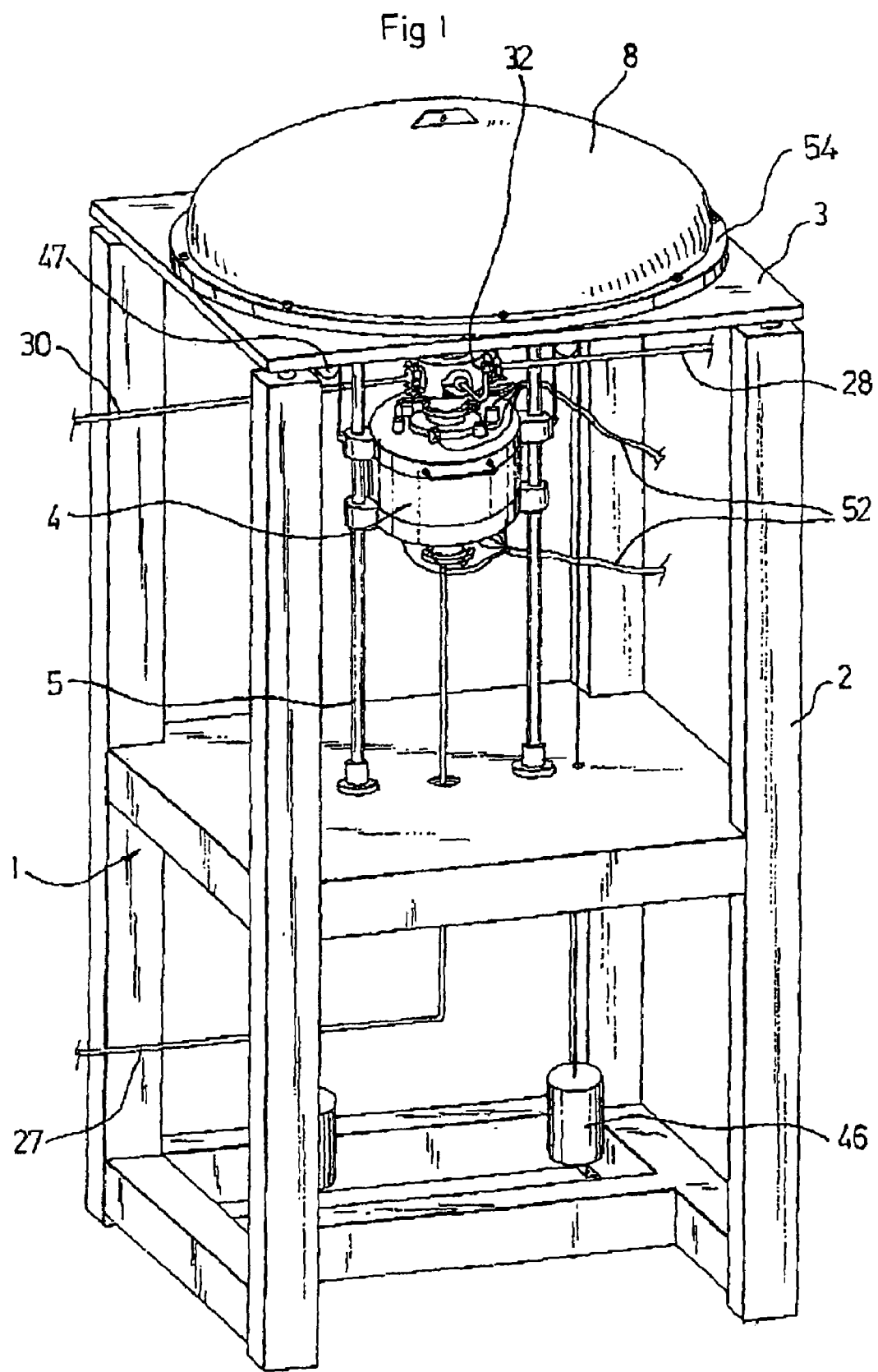
FIG. 1 is a diagrammatic view in perspective of a thermogravimetric test device according to the invention.

The device shown in FIG. 1 comprises a frame 1 formed of four vertical members 2 and various crosspieces and a plate providing rigidity for the frame. At their feet, the vertical members 2 have absorbent means (not shown), which are suitable for absorbing any shocks or vibrations transmitted to the device by the ground, in order to avoid any disturbance to the measurements. The frame also comprises a support plate 3 for the weighing means, to which a plurality of balances are fixed.

Figure 2:
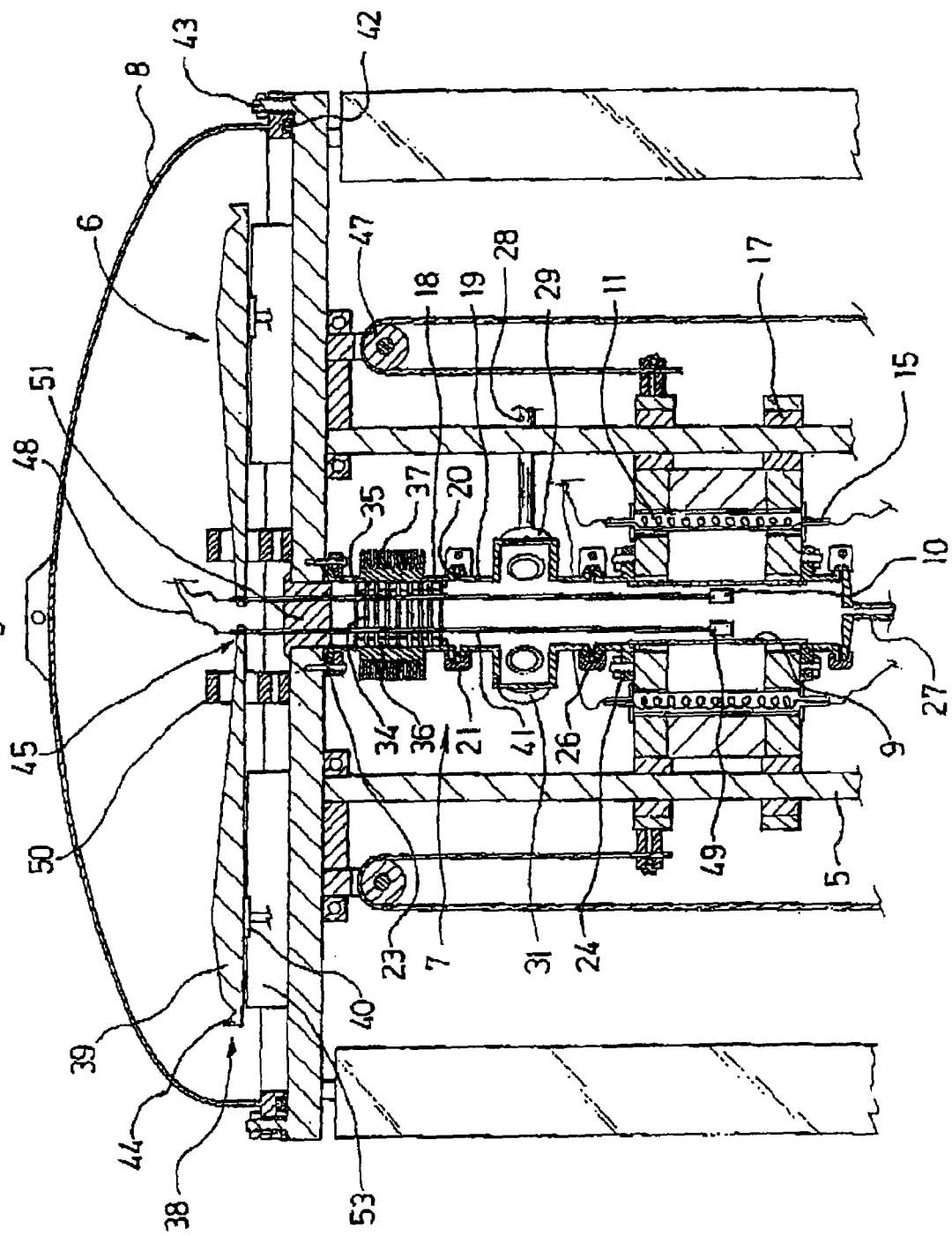
FIG. 2 is a diagrammatic vertical section of part of a thermogravimetric test device according to the invention.

The device shown comprises a furnace 4 (see also FIG. 4) which is mounted to slide on two vertical guide rails 5. To that end, the furnace has two pairs of lateral bearings 17 fixed to its substantially cylindrical body. The furnace 4 is associated, by way of two bearings 47 fixed beneath the support plate 3, with two counterweights 46 allowing on the one hand sliding manoeuvres of the furnace to be facilitated and on the other hand the furnace to be maintained in equilibrium whatever its position along the guide rails 5. The furnace is manoeuvred especially between a bottom preparation position, allowing access to the samples 10, and a top test position as shown in FIGS. 1 and 2, in which it is coupled in an air-tight manner to a confinement column 7.

Figure 4:
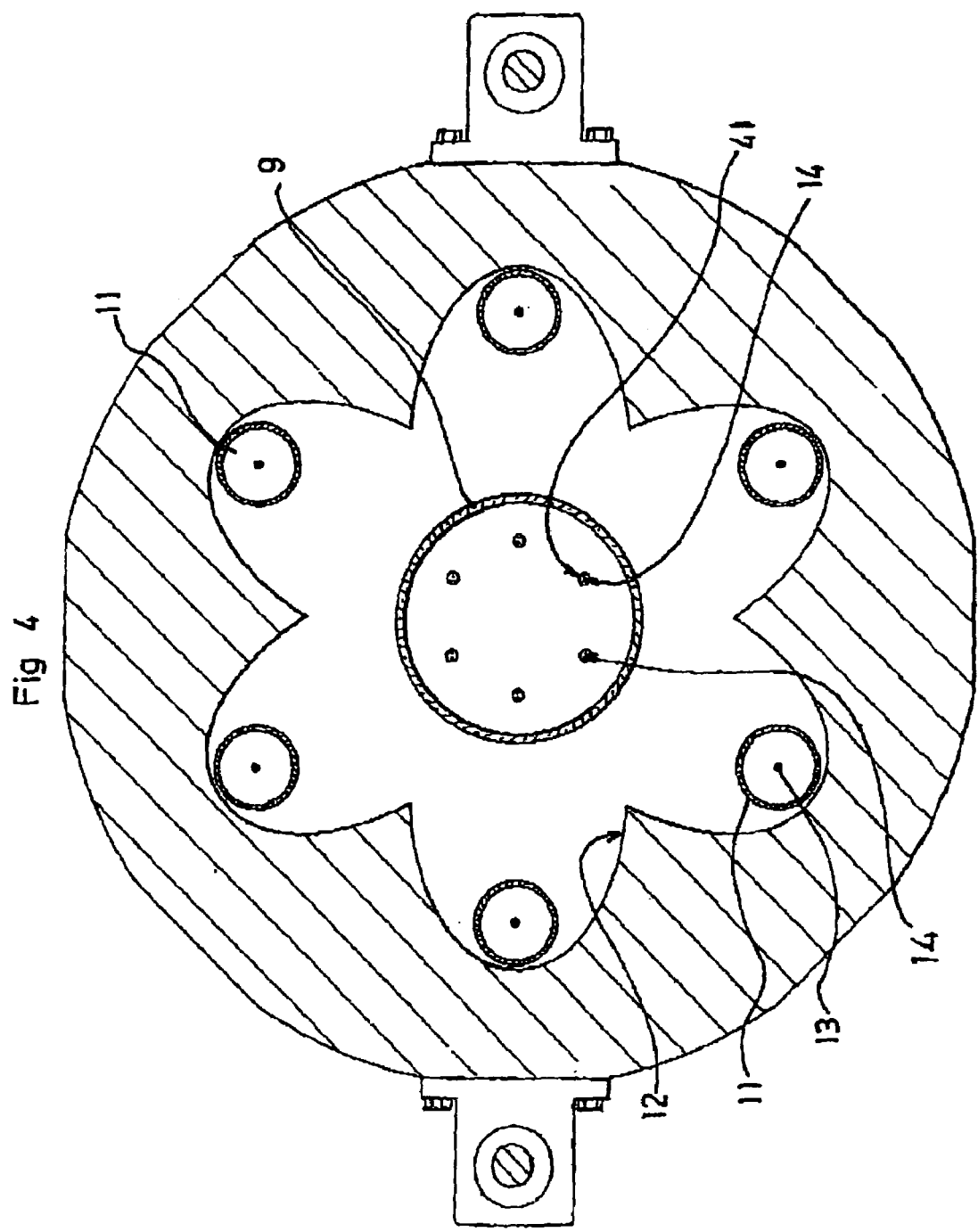
FIG. 4 is a diagrammatic horizontal section of a furnace according to the invention.

The furnace 4, shown in FIG. 4, is cylindrical in shape overall and has an inner face 12 forming six ellipse portions (in any horizontal cutting plane), the large axes of which extend substantially according to regularly spaced radii of the cylinder in order to define the branches of a star. In other words, the furnace has rotational symmetry modulo 60°, about a longitudinal axis of the furnace (also corresponding to a central axis of the device).

At the site of the focus 13 of each ellipse (ellipse focus that is furthest from the centre of the furnace) there is arranged a lamp 11 of the halogen lamp type. The focus 13 is called the emitting focus. Each lamp 11 is connected by sockets 15 and cables 52 to power supply and control means (not shown) comprising PID-type means for regulating the supply signal, in order to regulate the temperature of the furnace (regulation of the luminous intensity of the lamps—by regulation of the electric intensity supplied to the lamps—and therefore the temperature of the samples).

The other ellipse focus, referenced 14, is intended to receive a sample of material. According to their emission direction, the rays emitted by a lamp 11 are either emitted directly in the direction of the receiving focus 14 (and of the sample) of the ellipse portion associated with said lamp, or are reflected by said ellipse portion in the direction of the receiving focus 14 and of the sample of that ellipse, or are reflected by another ellipse portion in the direction of another focus, onto another sample. In this manner, all the rays emitted by the six lamps 11 converge towards the six receiving focuses 14. The site of each focus 14 defines, over the entire height of the lamps, a zone of maximum illumination where the rays emitted by the lamps 11 converge.

The six ellipses have separate receiving focuses, so that the furnace is able to accept six samples simultaneously. Each sample is heated by all of the lamps 11 and, in a more negligible manner, by the radiation emitted by the other hot samples. It is possible to adjust the temperature of a sample 10 in a precise manner by regulating the luminous intensity of a single lamp 11, especially of the lamp situated on the same ellipse, but this regulation must take into account the luminous intensity of the other lamps at that time.

The furnace also comprises a chamber 9 of optical-grade quartz, which chamber 9 defines the inner space of the furnace which is intended to receive the samples and inside which the controlled atmosphere is created.

Figure 3:
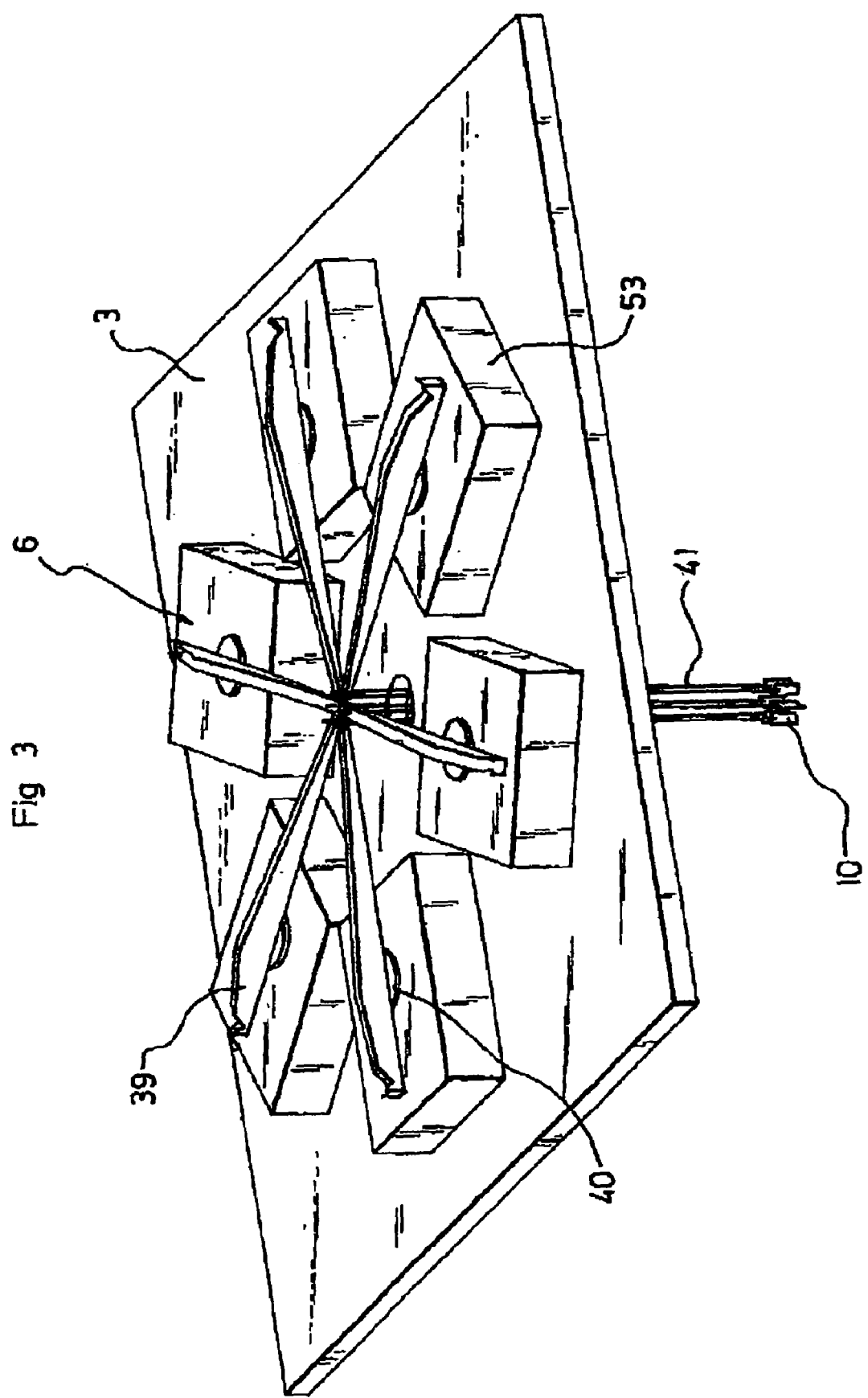
FIG. 3 is a diagrammatic view in perspective of weighing means according to the invention.

The device also comprises weighing means 6 comprising six independent balances 38 which are arranged in the shape of a star on the support plate 3 above the furnace 4, as shown in FIG. 3. The weighing means therefore have, inside the furnace, rotational symmetry modulo 60°.

Each balance comprises a balance arm 39 which extends radially above an ellipse of the furnace 4 and is fixed to an electronic weighing cell 40 integrated into an electronic casing 53. The cell 40 is a cell known per se (it will therefore not be described or shown in detail in the present patent) capable of measuring a total weight (balance arm 39, suspension rod 41, sample 10 and optional counterweight for equilibration of the balance arm) of less than 80 g with an error of 10 µg, including when it is subjected to a torque (especially in the absence of a counterweight). Such a cell is marketed especially under the trade mark SARTORIUS®.

At its central longitudinal end 45, called the measuring end, the balance arm 39 carries a suspension rod 41. The rod has a length such that, when the furnace is in the test position, locked on the confinement column 7, its lower end equipped with a sample 10 is located at a median height of the furnace 4. At its lower end, the rod 41 has a hook 49 by means of which a sample 10 is attached. The rod 41, which is preferably made of aluminium, also has two longitudinal channels which receive thermocouple wires 48 connected to the PID regulating means of the furnace. Said wires pass through the suspension rod to its lower end, from where they emerge close to the sample 10 in order to measure the temperature prevailing there.

Each balance also comprises a fixed double stop 50 which allows the angular displacement of the balance arm 39 to be limited in both directions, in order to avoid any risk of damage to the weighing cell 40 during handling of the device, and especially during attachment of a sample to the suspension rod 41 or the removal of a sample.

During operation, the six balances are covered by a single bell 8 for isolating them from the ambient environment. The bell 8 is fixed to the support plate 3 by means of a peripheral fixing flange 54. The flange comprises a lower recess for receiving a seal 42, and a plurality of bores suitable for each receiving a threaded rod 43 projecting from the support plate 3. Each rod 43 has an associated screw in order to keep the bell firmly flattened against the support plate.

The device also comprises a confinement column 7 in two portions: an upper portion 18, called the insulating portion, having means for limiting gaseous and thermal exchanges between the furnace and the balances, and a lower portion 19, called the branching portion, having branches for connection to means for generating the controlled gaseous atmosphere. The upper insulating portion 18 is fixed in an air-tight manner to the support plate 3, by means of a flange 23 screwed to the lower face of said plate and equipped with a seal. The lower branching portion 19 is fixed, at its upper end, to the lower end of the insulating portion 18 by means of a clamping flange 21 having conical bevels, allowing the opposite edges of said portions, between which there is interposed a seal 20, to the flattened against one another. The lower end of the branching portion 19 is fixed in a similar manner, by means of clamping flange 26 and a seal, to a fixing collar 24 of the furnace, when the furnace is in the test position. Following a test, the fixing flange 26 is removed to allow the furnace to slide downwards and to permit access to the samples.

The lower portion 19 comprises a first branch 29 for the connection of a gas inlet pipe 28, a second branch 31 for the connection of a pipe 30 of a vacuum pump (not shown), a third branch opening at a safety valve 32 (see FIG. 1), and a fourth branch provided for connecting another device (second gas inlet, measuring device, etc.) if required. Said branches are produced by any suitable means allowing the apparatus in question to be connected in an air-tight and optionally removable manner to the confinement column 7.

Figure 5:
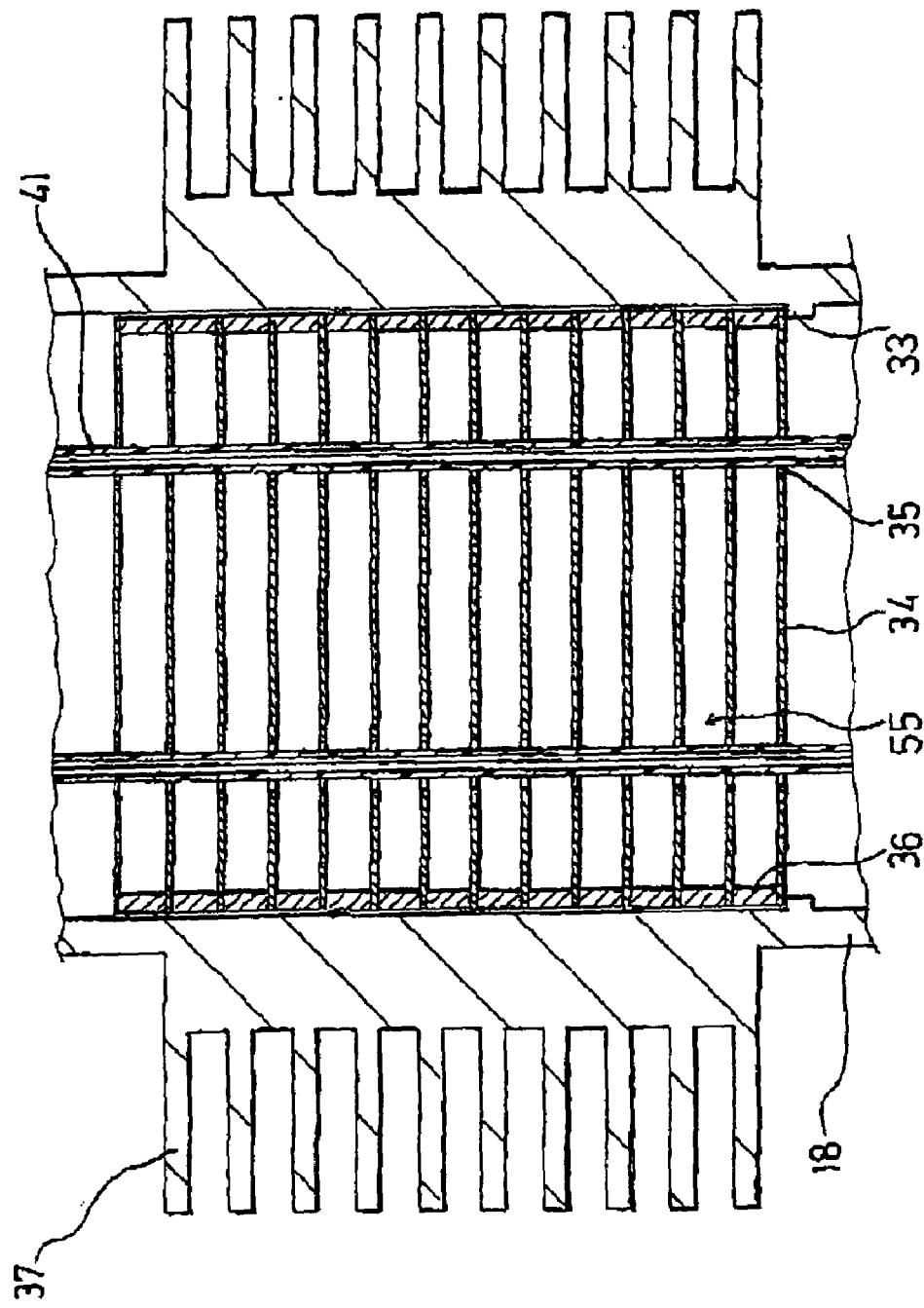
FIG. 5 is a diagrammatic vertical section of means, according to the invention, for limiting gaseous and thermal exchanges between the furnace and the weighing means.

The upper insulating portion 18, shown in FIG. 5, comprises a cylindrical pipe provided with outer transverse blades 37 for cooling it (these blades limit thermal exchanges by conduction in the wall of the pipe and increase the area of exchange by radiation with the ambient atmosphere), and a series of inner plates 34, the surface area of which corresponds to the inside section of the cylindrical pipe and which are separated by rings 36. The plates 34 and rings 36 are stacked on a shoulder 33 of the pipe. Each plate 34 has six holes 35 for the passage of the suspension rods 41. During the heating steps and at least part of the cooling steps of the cyclic test, the gases present in the chamber 9 of the furnace have a temperature greater than that of the gases present beneath the bell 8. They therefore ascend, by way of the confinement column 7, to the weighing means. The presence of the plates 34 allows the phenomena of convection—which are liable to disturb the measurements of the balances—between the furnace and the containment in which the balances are arranged, to be limited, while allowing gaseous exchanges of weak flow between said furnace and said containment in order to obtain a substantially identical ambient pressure between these two parts of the device (a pressure difference would act on the balances and falsify the measurements). It also allows the gases coming from the furnace and escaping towards the weighing means to be cooled: two successive plates in effect form a cooling chamber 55 into which the gases coming from the furnace 4 enter through the holes 35 and expand. The plates 34 preferably have faces of low emissivity in order also to reduce thermal exchanges by radiation between two consecutive plates. The use of a plurality of such plates allows the atmosphere prevailing beneath the bell 8 to be insulated thermally, in an effective manner and with a reduced space requirement, from the atmosphere of the furnace 4. The device also comprises, optionally, a plug 51 pierced with six holes for the passage of the rods 41, which plug 51 seals off a central hole of the support plate 3.

According to the invention, the device shown is used as follows:
- the furnace is placed in the bottom position in order to allow samples 10 to be attached to the suspension rods 41; it is to be noted that it is possible to attach a plurality of samples to the same rod within the limits of the capacities of the balance, but this is not desirable in so far as the measuring accuracy obtained is generally less good,
- the furnace is slid into its test position, and the furnace is coupled to the column 7 in an air-tight manner by means of the clamping flange 26; the chamber 9 of the furnace, the confinement column 7, the support plate 3 and the bell 8 then form a confined containment with a controlled atmosphere,
- an atmosphere is generated within the containment: depending on the material being tested, the vacuum is produced inside the containment by means of the vacuum pump and/or a gas, for example a corrosive gas, is introduced into the containment via the gas inlet pipe 28; the introduction can be carried out bubble by bubble if a very low pressure (primary or secondary vacuum) is desired inside the containment (and has been produced by means of the vacuum pump); the gas introduced is evacuated via the gas outlet pipe 27 in the lower portion of the chamber 9 of the furnace;
- the samples are subjected to predetermined thermal cycles as defined above: the electric intensity delivered to the lamps 11 is adjusted in real time by the PID regulating means as a function of the programmed thermal cycles and the actual temperature of the samples as measured by the thermocouples 48; the regulation can be carried out on each lamp independently or on several lamps jointly; the atmosphere generated is monitored at all times throughout the test, and it is possible to alter the atmosphere generated (in terms of pressure and/or chemical composition) during the test, and especially from one cycle to another or during the same cycle, or even during each cycle;

during each thermal cycle, the weight of each sample 10 as measured by the associated balance 38 is recorded continuously (in a memory of the computer means for controlling said balances, not shown) at least during the high-temperature stage, or even continuously throughout the test.

Following the test (for example after 3000 consecutive cycles), the furnace is detached from the confinement column 7 and is displaced to a preparation position in order to remove the samples.

The recorded weight measurements are transmitted to processing computer means (which may or may not be an integral part of the device) so that they can be presented, especially in the form of graphs (such as a graph showing the variation in mass Δm of a sample as a function of time), and/or analysed and/or applied to simulation software means.

FIG. 6 shows a variant of the weighing means and of the means for monitoring and regulating the furnace. Each balance 6 comprises a permanent counterweight 56 attached to the longitudinal end 44 of the balance arm, opposite its measuring end 45 and called the calibrating end, inside the protective bell 8. The counterweight is chosen to be of an inert material and to have a weight slightly greater than the typical weight of a sample.

Before the start of a test, the balance arm is equilibrated so as to adjust the balance to zero, by means of a tare 59 attached to the suspension rod 41. This operation results in better reliability of the weight measurements, the balance not being subjected to torque which might prejudice the accuracy of the measurements. The tare 59 is chosen to be of an inert material in order to have a constant weight throughout the test. The hook for receiving the tare is located beneath the containment column 7 so as to be accessible when the furnace is in the bottom preparation position.

In this manner it is not necessary to remove the protective bell 8 or to open the confinement column 7 in order to carry out equilibration of the balance before a test. The volume containing the weight-measuring instruments therefore remains confined between two tests. This confinement is not completely air-tight because exchanges of gas of weak flow with the outside can occur by way of the holes 35 for the passage of the suspension rods 41. However, it is sufficient to protect the measuring instruments 39, 40, 53, etc. from dust and from any thermal shock or any sudden variation in pressure, which might damage them. This adds to the durability of these instruments, which are particularly sensitive and fragile, and ensures that the weight measurements remain reliable test after test.

In addition, the device shown in FIG. 6 has six rigid rods 60 for supporting six controls 57. The controls 57 are pieces made of the same material as the samples to be tested or of a material having identical thermal properties (capacity, conductivity, absorptivity, emissivity, etc., it being necessary for the samples and the controls to have substantially the same temperature if they are subjected to the same radiation energy).

Each support rod 60 extends plumb with a suspension rod 41 in order to allow a control 57 to be placed below and in the immediate proximity of a sample 10, on a receiving focus 14 of the furnace. The control is therefore subjected strictly to the same radiation as the sample directly above it. The temperatures of the control and of the sample are therefore identical.

Each support rod 60 is hollow, so that it can receive thermocouple wires 58, which pass through the bottom of the furnace in an air-tight manner and are connected to the PID regulating means of the furnace. The suspension rods 41 for the samples therefore do not have thermocouple wires, which again contributes to greater accuracy of the weight measurements.

The measuring end of each thermocouple wire 58 is embedded inside the control 57 in a corresponding recess provided for that purpose, so that the temperature detected corresponds exactly to the temperature of the material (of the control and of the sample) and not to the temperature of the atmosphere close to a sample. It is possible in this manner to control the heating means accurately in order to carry out the programmed cycles.

Many variations of the invention compared with the embodiments shown and described are possible.

In particular, the number N of samples tested simultaneously is not limited to six (as shown). The number is, however, dictated by the desired use of the device (study, research, industrial validation tests, statistical studies, etc.), the maximum space available for accommodating the device, and the space available for the balances used. Owing to its overall star-shaped structure, the device according to the invention as shown is particularly compact.

In addition, the type of balance used is not limited to that shown (balance having an electronic weighing cell, balance with optoelectronic or magnetic means for measuring the displacement of the balance arm, etc.) and one device may incorporate balances of different types.

The required accuracy for each balance depends on the nature of the material being tested and the environmental and thermal conditions of the test. An error of less than 100 μg allows a large majority of tests to be carried out; an error of less than 10 μg is suitable for the most difficult tests (such as tests of oxidation of superalloys for the aviation industry).

Moreover, the means for measuring the temperature of the furnace and of the samples are not limited to those shown. The device may comprise a central pipe for the passage of thermocouple wires extending between the support plate of the balances and the chamber of the furnace, in the middle of the suspension rods, and passing through the insulating plates 34. By way of variation, temperature sensors equipped with wireless data transmission means are provided in the chamber of the furnace, in the immediate proximity of the samples. By way of variation, one of the samples is used as temperature control: it is attached to a suspension rod (such as 41) through which thermocouple wires pass (the other suspension rods being without thermocouples); and the measurements of the weight or variations in weight of that sample are not taken into account in subsequent studies. By way of variation, the only rod incorporating thermocouples is left free (it does not carry a sample).

The invention claimed is:

1. A method for thermogravimetrically testing the behaviour of a solid material in the presence of a controlled gaseous atmosphere, wherein:
a plurality of samples (10) are placed in the presence of said gaseous atmosphere inside the same controlled-atmosphere furnace (4),
each sample has its own associated balance (38) having an error of less than 100 µg,
the samples (10) are subjected to successive predetermined thermal cycles each comprising a heating step, during which the samples are heated directly, and a cooling step, during which the samples are not heated,
the weight of each sample is measured and recorded independently, in a continuous manner, at least during a high-temperature stage of the heating step of each thermal cycle.

2. The method as claimed in claim 1, wherein, in each thermal cycle, the samples (10) are heated so that their temperature is from 400° C. to 1800° C. at least during a high-temperature stage of the heating step.

3. The method as claimed in claim 1, wherein, in each thermal cycle, the samples (10) are heated so that their temperature is greater than 1100° C. at least during a high-temperature stage of the heating step.

4. The method as claimed in claim 1, wherein, in each thermal cycle, the samples (10) are heated at a rate of heating greater than 300° C. minute.

5. The method as claimed in claim 1, wherein, in each thermal cycle, the samples (10) are cooled at a rate of cooling greater than 100° C. minute.

6. The method as claimed in claim 1, wherein the samples (10) are subjected to thermal cycles each comprising a heating step, which consists of a phase of rise in temperature having a duration of less than 5 minutes and a high-temperature stage having a duration of the order of 60 minutes, and a cooling step, which consists of a phase of fall in temperature having a duration of less than 10 minutes and a low-temperature stage having a duration of from 0 to 15 minutes.

7. The method as claimed in claim 1, wherein the samples (10) are subjected to a number of successive thermal cycles of from 10 to 3000.

8. A device for thermogravimetrically testing the behaviour of a solid material in the presence of a controlled gaseous atmosphere, comprising:
a furnace (4) having a controlled gaseous atmosphere,
means (6) for weighing the material placed in the furnace, having an error of less than 100 µg,
confining means (7, 8, 34) suitable for limiting any disturbance to the weighing means owing to the external environment of the device and/or the controlled gaseous atmosphere,
wherein
the furnace (4) is suitable for receiving a number N, which is strictly greater than 1, of samples (10) of the material,
the furnace comprises means (11) for heating the samples directly, which means are capable of subjecting the samples to successive predetermined thermal cycles each comprising a heating step, during which the samples are heated, and a cooling step, during which the samples are not heated, the heating means being capable of imposing high-temperature stages during the heating steps,
the weighing means comprise N independent balances (38) having an error of less than 100 µg, each balance being capable of measuring and recording the weight of a sample continuously at least during a high-temperature stage of the heating step of each thermal cycle,
the device has a star-shaped structure overall, in which at least the balances are arranged in the shape of a star, which star-shaped structure is suitable for receiving the samples close to one another in a central portion of the furnace.

9. The device as claimed in claim 8, wherein the direct heating means (11) are capable of bringing the samples to a temperature greater than 1100° C.

10. The device as claimed in claim 8, wherein the direct heating means (11) are capable of heating the samples at a rate of heating greater than 300° C. minute.

11. The device as claimed in claims 8, wherein the direct heating means (11) are capable of cooling the samples at a rate of cooling greater than 100° C. minute.

12. The device as claimed in claim 8, wherein the direct heating means (11) are capable of carrying out thermal cycles each comprising a heating step, which consists of a phase of rise in temperature having a duration of less than 5 minutes and a high-temperature stage having a duration of the order of 60 minutes, and a cooling step, which consists of a phase of fall in temperature having a duration of less than 10 minutes and a low-temperature stage having a duration of from 0 to 15 minutes.

13. The device as claimed in claim 8, wherein the direct heating means (11) are capable of carrying out more than 3000 successive thermal cycles.

14. The device as claimed in claim 8, wherein each balance (38) has an error of less than 10 µg.

15. The device as claimed in claim 8, wherein each balance (38) has a drift of less than 1 µg/h.

16. The device as claimed in claim 8, wherein the balances (38) are mounted on the same support plate (3).

17. The device as claimed in claim 8, which comprises means (60) for supporting at least one piece of material (57), called a control, which means are suitable for holding the control in the immediate proximity of a sample (10) and are equipped with means (58) for measuring the temperature inside the control.

18. The device as claimed in claim 17, which comprises means (60) for supporting N controls, which means are suitable for holding a control beneath each sample, on its receiving focus, and are equipped with means (58) of the thermocouple wire type which end inside the control, for measuring independently the temperature of each of the controls.

19. The device as claimed in claim 8, wherein the furnace (4) is mounted to slide according to a substantially vertical direction between a bottom preparation position, in which it is located beneath the lower end of the suspension rods (41) in order to allow samples to be attached and/or removed, and a top test position, in which the lower end of the suspension rods (41) extends inside the chamber (9) of the furnace.

20. The device as claimed in claim 8, wherein the confining means comprise an upper protective bell (8) which is suitable for covering all of the balances (38) and for being fixed in a removable and air-tight manner to the support plate (3).

21. The device as claimed in claim 8, wherein the confining means (7) comprise a confinement column between the support plate (3) and the furnace (4), which column is suitable for producing, on the one hand, an air-tight and removable connection, allowing the suspension rods to pass and be confined, between the support plate and the chamber of the furnace, and, on the other hand, an air-tight connection, by means of branches (29, 31), to means for generating the controlled gaseous atmosphere.

22. The device as claimed in claim 8, wherein the means for generating the controlled gaseous atmosphere comprise, on the one hand, a vacuum pump and a gas inlet pipe (28) which are each connected to a branch (29) of the confinement column, and, on the other hand, a gas outlet pipe (27) which opens at a lower face of the chamber (9) of the furnace.

23. The device as claimed in claim 8, wherein the confining means comprise means (34, 36, 37) for limiting gaseous and thermal exchanges between the furnace and the weighing means, said limiting means comprising a plurality of superposed and distant plates (34) which are integrated into the confinement column (7) above the branches thereof and which delimit a plurality of successive cooling chambers (55), each plate being pierced with N holes (35) for the passage of the suspension rods.

24. The device as claimed in claim 23, wherein each plate (34) has faces of low emissivity.

25. The device as claimed in claim 8, wherein the furnace (4) comprises temperature-regulating means of the PID type.

26. The device as claimed in claim 8, wherein the furnace comprises temperature-regulating means suitable for controlling each lamp (11) independently.

27. The device as claimed in claim 8, wherein the furnace comprises at least N high-radiation lamps (11), a chamber (9) for receiving the samples, made of a thermal resistant material that is transparent to the radiation of the lamps, and a reflective peripheral inner face (12) having a shape that is suitable for defining at least N separate zones of maximum illumination inside the chamber, at the site of which the samples may be placed.

28. The device as claimed in claim 27, wherein the peripheral inner face (12) of the furnace forms at least, a N ellipse portions arranged in a star, each ellipse having a first focus (13) outside the chamber (9), called the emitting focus, at the site of which there is arranged a lamp, and a second focus (14) inside the chamber, called the receiving focus, at the site of which a sample may be placed, at least N of said ellipses having separate receiving focuses.

29. The device as claimed in claim 28, wherein the chamber (9) and the receiving focuses (14) are situated in the central portion of the furnace and the emitting focuses (13) are situated in the peripheral portion of the furnace, and wherein the chamber (9) has reduced radial dimensions.

30. The device as claimed in claim 8, wherein the balances (38) are arranged above the furnace and each comprise a balance arm (39), means (40) for measuring a displacement or a force to which the balance arm is subjected, and a suspension rod (41) of aluminium which extends substantially vertically and has a lower end provided with a hook (49) for the attachment of a sample (10) and an upper end articulated with or fixed to a longitudinal end (45) of the balance arm, called the measuring end.

31. The device as claimed in claim 30, wherein the balance arms (39) of the N balances are arranged in the shape of a star, each balance arm extending substantially according to a radial direction so that its measuring end (45) hangs over the central portion of the furnace.

32. The device as claimed in claim 30, wherein the suspension rods (41) are of the capillary type having two channels in order to permit the passage of thermocouple wires (48).

33. The device as claimed in claim 30, wherein the measuring means of at least one balance comprise an electronic weighing cell (40) to which the balance arm (39) is fixed.

34. The device as claimed in claim 30, wherein each balance comprises a permanent counterweight (56) fixed to one longitudinal end (44) of the balance arm, called the calibrating end, so as to be suspended inside the protective bell (8).

\* \* \* \* \*